United States Patent [19]

Malherbe et al.

[11] Patent Number: 4,547,537

[45] Date of Patent: Oct. 15, 1985

[54] N-PIPERIDYL TETRAHYDRO-1,4-OXAZIN-2-ONE LIGHT STABILIZERS

[75] Inventors: Roger F. Malherbe, Basel, Switzerland; Michael H. Ackerman, East Meadow, N.Y.

[73] Assignee: Ciba-Geigy Corporation, Ardsley, N.Y.

[21] Appl. No.: 637,240

[22] Filed: Aug. 2, 1984

[51] Int. Cl.[4] .................... C08K 5/34; C07D 413/00; C07D 29/30

[52] U.S. Cl. ...................................... 524/97; 544/130; 546/209

[58] Field of Search ................. 524/97, 96; 544/129, 544/130; 546/209

[56] References Cited

U.S. PATENT DOCUMENTS

| | | | |
|---|---|---|---|
| 2,306,779 | 12/1942 | Coleman | 524/97 |
| 3,413,259 | 11/1968 | Blümell et al. | 524/97 |
| 3,514,456 | 5/1970 | Makanishi et al. | 544/129 |
| 3,586,678 | 6/1971 | Kühnis et al. | 544/130 |

Primary Examiner—John Kight
Assistant Examiner—Kriellion Morgan
Attorney, Agent, or Firm—Luther A. R. Hall

[57] ABSTRACT

Compounds of the formula L-T, where L is an unsubstituted or substituted tetrahydro-1,4-oxazine-2-one group and T is a substituted 4-piperidinyl hindered amine moiety, are effective light stabilizers for polyolefins and other organic polymers.

19 Claims, No Drawings

N-PIPERIDYL TETRAHYDRO-1,4-OXAZIN-2-ONE LIGHT STABILIZERS

BACKGROUND OF THE INVENTION

The present invention pertains to compounds containing a tetrahydro-1,4-oxazin-2-one group in combination with a substituted 4-piperidinyl hindered amine moiety which are useful as light and heat stabilizers for organic materials and to stabilized compositions containing said compounds.

The hindered amine compounds having the 2,2,6,6-tetra-substituted piperidinyl structure have long been known as effective light stabilizers for organic materials and have enjoyed considerable commercial success.

Such hindered amine light stabilizers are described in detail by H. J. Heller and H. R. Blattmann, Pure and Applied Chemistry, 36, 141–161 (1973).

It is known from U.S. Pat. Nos. 3,850,877 and 4,033,928 that esters and amides of substituted 2,2,6,6-tetramethylpiperidine are good light stabilizers for polymeric substrates, particularly polyolefins and epoxy resins.

Polyalkylated 4-aminopiperidine derivatives are known to be useful as light and heat stabilizers for synthetic polymers.

In U.S. Pat. No. 3,684,765, 4-aminopiperidine derivatives having the formula I are disclosed:

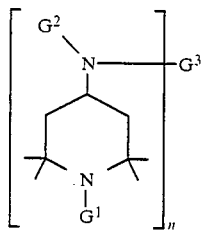

wherein $G^1$ represents hydrogen or an acyl group; $G^2$ represents hydrogen, an unsubstituted or substituted alkyl group, a cycloalkyl group, an unsubstituted or substituted aryl group; $G^3$ represents hydrogen, an alkoxycarbonyl group or a mono-, di- or trivalent acyl, carbonyl or thiocarbamoyl groups.

Compounds where $G^2$ and $G^3$ together are selected heterocyclic rings are disclosed in U.S. Pat. Nos. 4,033,928, 4,298,737 and 4,309,546 and U.S. Pat. No. 4,472,547.

None of these patents disclose or suggest compounds having a tetrahydro-1,4-oxazin-2-one moiety attached to a substituted piperidinyl hindered amine group.

The instant compounds possess excellent stabilization properties coupled with good solubility, and thermal and hydrolytic stability.

DETAILED DISCLOSURE

This invention relates to compounds containing a tetrahydro-1,4-oxazine-2-one group in combination with a substituted 4-piperidinyl hindered amine moiety which are useful as light stabilizers for organic polymers and to stabilized compositions containing said compounds.

The instant invention more particularly pertains to a light stabilizer compound of the formula I $$L-T \quad (I)$$

wherein
L is a tetrahydro-1,4-oxazin-2-one group of the formula

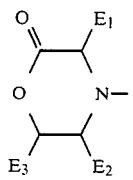

$E_1$ is hydrogen, alkyl of 1 to 16 carbon atoms or phenyl,
$E_2$ is hydrogen, alkyl of 1 to 4 carbon atoms or phenyl,
$E_3$ is hydrogen or methyl,
T is a group of the formula

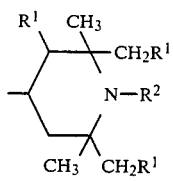

with L attached to the 4-position of the piperidinyl ring,
$R^1$ is hydrogen or alkyl of 1 to 5 carbon atoms, and
$R^2$ is hydrogen, oxygen, hydroxyl, alkyl of 1 to 12 carbon atoms, alkenyl of 3 to 8 carbon atoms, propargyl, benzyl, cyano, hydroxyalkyl of 2 to 4 carbon atoms, alkanoyl of 2 to 10 carbon atoms, alkenoyl of 3 to 4 carbon atoms, benzoyl, alkoxy of 1 to 8 carbon atoms, alkanoyloxy of 2 to 10 carbon atoms, alkenoyloxy of 3 to 4 carbon atoms or benzoyloxy.

The instant compounds contain a tetrahydro-1,4-oxazin-2-one group L of formula

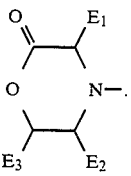

When $E_1$ is alkyl of 1 to 16 carbon atoms, $E_1$ may be, for example, methyl, ethyl, isopropyl, n-butyl, n-amyl, 2-ethylhexyl, n-decyl, n-dodecyl or n-tetradecyl.

When $E_2$ is alkyl of 1 to 4 carbon atoms, $E_2$ is, for example, methyl, ethyl, n-propyl or n-butyl.

Preferably $E_2$ is hydrogen.

Most preferably $E_1$, $E_2$ and $E_3$ are each hydrogen.

T is derived from a substituted 4-aminopiperidine where $R^1$ is hydrogen or alkyl of 1 to 5 carbon atoms such as, for example, methyl, ethyl, n-butyl or n-amyl. Preferably $R^1$ is hydrogen or methyl, and most preferably $R^1$ is hydrogen.

$R^2$ may be hydrogen, oxygen, hydroxyl or alkyl of 1 to 12 carbon atoms such as, for example, methyl, ethyl, isopropyl, sec-butyl, n-amyl, 2-ethylhexyl, n-decyl or n-dodecyl, preferably alkyl of 1 to 4 carbon atoms.

$R^2$ may also be alkenyl of 3 to 8 carbon atoms such as, for example, allyl, butenyl, crotyl or octenyl, preferably allyl.

When $R^2$ is hydroxyalkyl, $R^2$ is, for example, 2-hydroxyethyl, 2-hydroxypropyl or 2-hydroxybutyl, preferably 2-hydroxyethyl.

$R^2$ is alkanoyl of 2 to 10 carbon atoms such as, for example, acetyl, propionyl, butanoyl, valeroyl, caproyl, capryloyl or decanoyl. Preferably $R^2$ as alkanoyl is acetyl.

$R^2$ is also alkenoyl of 3 or 4 carbon atoms such as, for example, acryloyl, methacryloyl or crotonoyl.

When $R^2$ is alkoxy of 1 to 8 carbon atoms, $R^2$ is, for example, methoxy, ethoxy, isopropoxy, n-butoxy, hexyloxy or octyloxy.

When $R^2$ is alkanoyloxy of 2 to 10 carbon atoms, $R^2$ is, for example, acetoxy, propionyloxy, butanoyloxy, valeroyloxy, octanoyloxy or decanoyloxy.

When $R^2$ is alkenoyloxy of 3 to 4 carbon atoms, $R^2$ is, for example, acryloyloxy, methacryloyloxy or crotonyloxy.

Preferably $R^2$ is hydrogen, oxygen, hydroxyl, alkyl of 1 to 4 carbon atoms, allyl, 2-hydroxyethyl, acetyl, propargyl, benzyl, cyano, benzoyl or benzoyloxy.

The intermediates needed to prepare the instant compounds are largely items of commerce or are easily prepared by known methods.

The synthesis of tetrahydro-1,4-oxazin-2-ones is reviewed in "Heterocyclic Compounds", Vol. 6, R. C. Elderfield, Ed., John Wiley, New York, 1957. These compounds are sometimes referred to as 2-morpholones.

Two general routes are used.

A. Substituted glycine ester is heated with an oxirane.

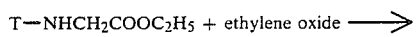

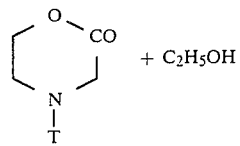

B. Substituted aminoethanol is heated with an alpha-halo ester in the presence of a base

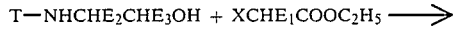

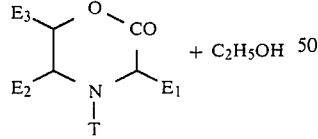

where X is chloro or bromo.

The instant compounds are most conveniently prepared by method B.

The intermediate N-piperidinyl aminoalcohols are readily available by reductive amination of triacetoneamine with the approximate aminoalcohol, as reported in U.S. Pat. No. 3,684,765. Another method is the hydroxyalkylation of the corresponding primary amine according to U.S. Pat. No. 4,166,813.

The compounds of this invention are effective light stabilizers in a wide range of organic polymers. Polymers which can be stabilized include:

1. Polymers which are derived from mono- or diolefins, e.g., polyethylene which can optionally be cross-linked, polypropylene, polyisobutylene, polymethylbutene-1, polymethylpentene-1, polyisoprene, polybutadiene.

2. Mixtures of the homopolymers cited under 1, for example mixtures of polypropylene and polyethylene, polypropylene and polybutene-1, polypropylene and polyisobutylene.

3. Copolymers of the monomers based on the homopolymers cited under 1, for example ethylene/propylene copolymers, propylene/butene-1, copolymers, propylene/isobutylene copolymers, ethylene/butene-1 copolymers as well as terpolymers of ethylene and propylene with a diene, for example hexadiene, dicyclopentadiene or ethylidene norbornene, and copolymers of α-olefins, e.g., ethylene with acrylic or methacrylic acid.

4. Polystyrene.

5. Copolymers of styrene and of α-methylstyrene, for example styrene/butadiene copolymers, styrene/acrylonitrile copolymers, styrene/acrylonitrile/methacrylate copolymers, styrene/acrylonitrile copolymers modified with acrylic ester polymers to provide impact strength as well as block copolymers, e.g., styrene/butadiene/styrene block copolymers.

6. Graft copolymers of styrene, for example the graft polymer of styrene to polybutadiene, the graft polymer of styrene with acrylonitrile to polybutadiene as well as mixtures thereof with the copolymers cited under 5, commonly referred to as acrylonitrile/butadiene/styrene or ABS plastics.

7. Halogen-containing vinyl polymers, for example polyvinyl chloride, polyvinylidene chloride, polyvinyl fluoride, polychloropropene, chlorinated rubbers, vinyl chloride/vinylidene chloride copolymers, vinyl chloride/vinyl acetate copolymers, vinylidene chloride/vinyl acetate copolymers.

8. Polymers which are derived from α,β-unsaturated acids and derivatives thereof, such as polyacrylates and polymethacrylates, polyacrylic amides and polyacrylonitrile.

9. Polymers which are derived from unsaturated alcohols and amines and from the acyl derivatives thereof or acetals, for example polyvinyl alcohol, polyvinyl acetate, polyvinyl stearate, polyvinyl benzoate, polyvinyl maleate, polyvinyl butyral, polyallyl phthalate, polyallyl melamine and copolymers thereof with other vinyl compounds, for example ethylene/vinyl acetate copolymers.

10. Homopolymers and copolymers which are derived from epoxides, for example polyethylene oxide or the polymers which are derived from bis-glycidyl ethers.

11. Polyacetals, for example polyoxymethylene, as well as polyoxymethylenes which contain ethylene oxide as comonomer.

12. Polyalkylene oxides, for example polyoxyethylene, polypropylene oxide or polybutylene oxide.

13. Polyphenylene oxides.

14. Polyurethanes and polyureas, such as in urethane coatings.

15. Polycarbonates.

16. Polysulfones.

17. Polyamides and copolyamides which are derived from diamines and dicarboxylic acids and/or from aminocarboxylic acids or the corresponding lactams, for example polyamide 6, polyamide 6/6, polyamide 6/10, polyamide 11, polyamide 12, poly-m-phenylene-isophthalamide.

18. Polyesters which are derived from dicarboxylic acids and dialcohols and/or from hydroxycarboxylic acids or the corresponding lactones, for example polyethylene glycol terephthalate, poly-1,4-dimethylolcyclohexane terephthalate.

19. Cross-linked polymers which are derived from aldehydes on the one hand and from phenols, ureas and melamine on the other, for example phenol/formaldehyde, urea/formaldehyde and melamine/formaldehyde resins.

20. Alkyl resins, for example glycerol/phthalic acid resins and mixtures thereof with melamine/formaldehyde resins.

21. Unsaturated polyesters resins which are derived from copolyesters of saturated and unsaturated dicarboxylic acids with polyhydric alcohols as well as from vinyl compounds as cross-linking agents and also the halogen-containing, flame-resistant modifications thereof.

22. Natural polymers, for example cellulose, rubber, as well as the chemically modified homologous derivatives thereof, for example cellulose acetates, cellulose propionates and cellulose butyrates and the cellulose ethers, for example methyl cellulose.

The stabilizing of polyolefins, styrene polymers and polyamides and of polyurethanes is of particular importance, and the instant copolymers are outstandingly suitable for this. Examples of such polymers are high density and low density polyethylene, polypropylene, ethylene/propylene copolymers, polystyrene, styrene/butadiene/acrylonitrile terpolymers, mixtures of polyolefins or of styrene polymers, and polyurethanes based on polyethers or polyesters, in the form of lacquers, filaments, films, sheets, elastomers or foams.

The instant stabilizers are added to the plastics in a concentration of 0.05 to 5% by weight, calculated relative to the material to be stabilized. Preferably, 0.1 to 2.5% by weight of the stabilizer calculated relative to the material to be stabilized, is incorporated into the latter.

Incorporation can be effected after polymerization, for example by mixing the compounds and, if desired, further additives into the melt by the methods customary in the art, before or during shaping, or by applying the dissolved or dispersed compounds to the polymer, with subsequent evaporation of the solvent if necessary.

The stabilizers can also be added to the plastics to be stabilized in the form of a master batch which contains these compounds, for example in a concentration of 2.5 to 25% by weight.

Although the compounds of the invention may be used to provide a light stabilizing function, the compounds of this invention are often combined with other stabilizers, even other light stabilizers, in the preparation of stabilized compositions. The stabilizers may be used with phenolic antioxidants, pigments, colorants or dyes, light stabilizers such as hindered amines, metal deactivators, etc.

In general, the stabilizers of this invention are employed from about 0.05 to about 5% by weight of the stabilized composition, although this will vary with the particular substrate and application. An advantageous range is from about 0.1 to about 2.5%.

The stabilizers of Formula I or II may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The stabilized polymer compositions of the invention may optionally also contain from about 0.05 to about 5%, preferably from about 0.1 to about 2.5% by weight of various conventional additives, such as the following, particularly phenolic antioxidants or light-stabilizers, or mixtures thereof:

1. Antioxidants 1.1 Simple 2,6-dialkylphenols, such as, for example, 2,6-di-tert.-butyl-4-methylphenol, 2-tert.-butyl-4,6-dimethylphenol, 2,6-di-tert.-butyl-4-methoxymethylphenol and 2,6-dioctadecyl-4-methylphenol.

1.2 Derivatives of alkylated hydroquinones, such as for example, 2,5-di-tert.-butyl-hydroquinone, 2,5-di-tert.-amyl-hydroquinone, 2,6-di-tert.-butyl-hydroquinone, 2,5-di-tert.-butyl-4-hydroxy-anisole, 3,5-di-tert.-butyl-4-hydroxy-anisole, 3,5-di-tert.-butyl-4-hydroxyphenyl stearate and bis-(3,5-di-tert.-butyl-4-hydroxyphenyl)adipate.

1.3 Hydroxylated thiodiphenyl ethers, such as for example, 2,2'-thio-bis-(6-tert.-butyl-4-methylphenol), 2,2'-thio-bis-(4-octylphenol), 4,4'-thio-bis-(tert.-butyl-3-methylphenol), 4,4'-thio-bis-(3,6-di-sec.-amylphenol), 4,4'-thio-bis-(6-tert.-butyl-2-methylphenol) and 4,4'-bis-(2,6-dimethyl-4-hydroxyphenyl)disulfide.

1.4 Alkylidene-bisphenols, such as, for example, 2,2'-methylene-bis-(6-tert.-butyl-4-methylphenol), 2,2'-methylene-bis-(6-tert.-butyl-4-ethylphenol), 4,4'-methylene-bis-(6-tert.-butyl-2-methylphenol), 4,4'-methylene-bis-(2,6-di-tert.-butylphenol), 2,6-di-(3-tert.-butyl-5-methyl-2-hydroxybenzyl)-4-methylphenol, 2,2'-methylene-bis-[4-methyl-6-(-methylcyclohexyl)-phenol], 1,1-bis(3,5-dimethyl-2-hydroxyphenyl)-butane, 1,1-bis-(5-tert.-butyl-4-hydroxy-2-methylphenyl)-butane, 2,2-bis-(3,5-di-tert.-butyl-4-hydroxyphenyl)-propane, 1,1,3-tris-(5-tert.-butyl-4-hydroxy-2-methylphenyl)-butane, 2,2-bis-(5-tert.-butyl-4-hydroxy-2-methylphenyl)-4-n-dodecylmercapto-butane, 1,1,5,5-tetra-(5-tert.-butyl-4-hydroxy-2-methylphenyl)-pentane and ethylene glycol bis-[3,3-bis-(3-tert.-butyl-4-hydroxyphenyl)-butyrate].

1.5 O-, N- and S-benzyl compounds, such as for example, 3,5,3',5'-tetra-tert.-butyl-4,4'-dihydroxydibenzyl ether, octadecyl 4-hydroxy-3,5-dimethylbenzyl-mercaptoacetate, tris-(3,5-di-tert.-butyl-4-hydroxybenzyl)-amine and bis-(4-tert.-butyl-3-hydroxy-2,6-dimethylbenzyl)dithioterephthalate.

1.6 Hydroxybenzylated malonates, such as for example, dioctadecyl 2,2-bis-(3,5-di-tert.-butyl-2-hydroxybenzyl)-malonate, dioctadecyl 2-(3-tert.-butyl-4-hydroxy-5-methylbenzyl)-malonate, di-dodecylmercapto-ethyl 2,2-bis-(3,5-di-tert.-butyl-4-hydroxybenzyl)-malonate and di-[4-(1,1,3,3-tetramethylbutyl)phenyl] 2,2-bis-(3,5-di-tert.-butyl-4-hydroxybenzyl)-malonate.

1.7 Hydroxybenzyl-aromatic compounds, such as, for example, 1,3,5-tri-(3,5-di-tert.-butyl-4-hydroxybenzyl)-2,4,6-trimethyl-benzene, 1,4-di-(3,5-di-tert-butyl-4-hydroxybenzyl)-2,3,5,6-tetramethylbenzene and 2,4,6-tri-(3,5-di-tert.-butyl-4-hydroxy-benzyl)-phenol.

1.8 s-Triazine compounds, such as, for example 2,4-bis-octylmercapto-6-(3,5-di-tert.-butyl-4-hydroxyanilino)-s-triazine, 2-octylmercapto-4,6-bis-(3,5-di-tert.-butyl-4-hydroxyanilino)-s-triazine, 2-octylmercapto-4,6-bis-(3,5-di-tert.-butyl-4-hydroxyphenoxy)-s-triazine, 2,4,6-tris-(3,5-di-tert.-butyl-4-hydroxyphenoxy)-s-triazine, 2,4,6-tris-(3,5-di-tert.-butyl-4-hydroxyphenylethyl)-s-triazine and 1,3,5-tris-(3,5-di-tert.-butyl-4-hydroxybenzyl)isocyanurate.

1.9 Amides of β-(3,5-di-tert.-butyl-4-hydroxyphenyl)-propionic acids, such as, for example 1,3,5-tris-(3,5,-di-tert.-butyl-4-hydroxyphenyl-propionyl)-hexahydro-s-triazine and N,N'-di-(3,5-di-tert.-butyl-4-hydroxyphenyl-propionyl)-hexamethylenediamine, N,N'-bis-β-(3,5-di-t-butyl-4-hydroxyphenyl)-propionyl-hydrazine.

1.10 Esters of β-(3,5-di-tert.-butyl-4-hydroxyphenyl)-propionic acid with monohydric or polyhydric alcohols, such as for example, with methanol, ethanol, octadecanol, 1,6-hexanediol;. 1,9-nonanediol, ethylene glycol, 1,2-propane-diol, diethylene glycol, thiodiethylene glycol, neopentylglycol, pentaerythritol, 3-thiaundecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo-[2.2.2]octane.

1.11 Esters of β-(5-tert.-butyl-4-hydroxy-3-methylphenyl)-propionic acid with monohydric or polyhydric alcohols, such as for example, with methanol, ethanol, octadecanol, 1,6-hexanediol, 1-9-nonanediol, ethylene glycol, 1,2-propanediol, di-ethylene glycol, thiodiethylene glycol, neopentylglycol, pentaerythritol, 3-thiaundecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo[2.2.2]octane.

1.12 Esters of 3,5-di-tert.-butyl-4-hydroxyphenylacetic acid with monohydric or polyhydric alcohols, such as for example, with methanol, ethanol, octadecanol, 1,6-hexandiol, 1,9-nonanediol, ethylene glycol, 1,2-propenediol, diethylene glycol, thiodiethylene glycol, neopentylglycol, pentaerythritol, 3-thia-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo[2.2.2]-octane, especially the tetrakis ester of pentaerythritol.

1.13 Benzylphosphonates, such as, for example, dimethyl 3,5-di-tert.-butyl-4-hydroxybenzylphosphonate, diethyl 3,5-di-tert.-butyl-4-hydroxybenzylphosphonate, dioctadecyl 3,5-di-tert.-butyl-4-hydroxybenzylphosphonate and dioctadecyl 5-tert.-butyl-4-hydroxy-3-methylbenzylphosphonate.

2. Light-stabilizers
2.1 Esters of optionally substituted benzoic acids, e.g., 3,5-di-tert.-butyl-4-hydroxybenzoic acid, 2,4-di-tert.-butylphenyl ester or -octadecyl ester or 2-methyl-4,6-di-tert.-butylphenyl ester.

2.2 Sterically hindered amines e.g., 4-benzoyl-2,2,6,6-tetramethylpiperidine, 4-stearyloxy-2,2,6,6-tetramethylpiperidine, bis-(2,2,6,6-tetramethylpiperidyl)sebacate, bis-(1,2,2,6,6-pentamethylpiperidyl)sebacate, bis-(1,2,2,6,6-pentamethylpiperidyl) 2-n-butyl-2-(2-hydroxy-3,5-di-tert-butylbenzyl)malonate or 3-n-octyl-7,7,9,9-tetra-methyl-1,3,8-triazaspiro[4.5]decane-2,4-dione.

2.3 Oxalic acid diamides, e.g., 4,4'-di-octyloxy-oxanilide, 2,2'-di-octyloxy-5,5'-di-tert.butyl-oxanilide, 2,2'-didodecyloxy-5,5'-di-tert.-butyl-oxanilide, 2-ethoxy-2'-ethyl-oxanilide, N,N'-bis-(3-dimethyl-aminopropyl)-oxalamide, 2-ethoxy-5-tert.-butyl-2'-ethyl-oxanilide and the mixture thereof with 2-ethoxy-2'-ethyl-5,4'-di-tert.-butyl-oxanilide, or mixture of ortho- and para-methoxy- as well as of o- and p-ethoxy-di-substituted oxanilides.

3. Metal deactivators, e.g., oxanilide, isophthalic acid dihydrazide, sebacic acid-bis-phenylhydrazide, bis-benzylidene-oxalic acid dihydrazide, N,N'-diacetal-adipic acid dihydrazide, N,N'-bis-salicyloyl-oxalic acid dihydrazide, N,N'-bis-salicyloylhydrazine, N,N'-bis-(3,5-di-tert.-butyl-4-hydroxyphenylpropionyl)-hydrazine, N-salicyloyl-N'-salicylalhydrazine, 3-salicyloyl-amino-1,2,4-triazole or N,N'-bis-salicyloyl-thiopropionic acid dihydrazide.

4. Basic co-stabilizers, e.g., alkali metal salts and alkaline-earth metal salts of higher fatty acids, for example Ca-stearate, Zn-stearate, Mg-behenate, Na-ricinoleate or K-palmitate.

5. Nucleation agents, e.g., 4-tert.-butylbenzoic acid, adipic acid or diphenylacetic acid.

6. Phosphites and phosphonites, such as, for example, triphenyl phosphite, diphenylalkyl phosphites, phenyldialkyl phosphites, tri-(nonyl-phenyl)phosphite, trilauryl phosphite, trioctadecyl phosphite and 3,9-isodecyloxy-2,4,8,10-tetraoxa-3,9-diphospha-[5.5]-undecane and tetra(2,4-di-tert-butylphenyl)diphenylene-4,4'-bis(phosphonite).

Other additives that can be incorporated in the stabilized compositions are thiosynergists such as dilauryl thiodiproprionate, lubricants such as stearyl alcohol, fillers, asbestos, kaolin, talc, glass fibers, pigments, optical brighteners, flameproofing agents and antistatic agents.

The following examples are presented for the purpose of illustration only and are not to be construed to limit the nature or scope of the instant invention in any manner whatsoever.

EXAMPLE 1

N-(2,2,6,6-Tetramethylpiperidin-4-yl)-tetrahydro-1,4-oxazin-2-one

To a mixture of 20.0 g (0.1 mole) of 2-(2,2,6,6-tetramethylpiperidin-4-yl-aminoethanol and 21.2 g (0.2 mole) of sodium carbonate is added over a three hour period of 120° C., 18.0 g (0.15 mole) of ethyl chloroacetate. Heating is continued for one more hour. The reaction mixture is then cooled to 25° C. and filtered.

The filtrate is then concentrated, and the product is distilled to give 15.3 g (64% yield) of a clear oil (b.p. 118°–125° C./0.1 mm), which solidified upon standing (m.p. 77°–85° C.).

IR (film): 1730 cm$^{-1}$ (C=O).

NMR (CDCl$_3$): δ = 1.03 (t, 2H); 1.12 (s, 3H); 1.21 (s, 3H); 1.75 (d x d, 2H); 2.78 (complex, 3H); 3.47 (s, 2H); 4.36 (t, 2H).

Anal. $C_{13}H_{24}N_2O_2$ (240.3): Calcd.: C, 65.0; H, 10.1; N, 11.7. Found: C, 65.0; H, 10.1; N, 11.7.

EXAMPLE 2

N-(2,2,6,6-Tetramethylpiperidin-4-yl)-tetrahydro-6-methyl-1,4-oxazin-2-one

Following the procedure of Example 1, the above-named compound is prepared when an equivalent amount of 1-(2,2,6,6-tetramethylpiperidin-4-ylamino)-propan-2-ol is used instead of 2-(2,2,6,6-tetramethylpiperdin-4-ylamino)ethanol. The material is obtained as a clear oil, b.p. 121°–127° C./0.05 mm.

The NMR and IR spectra were consistent with the structure.

Anal. $C_{14}H_{26}N_2O_2$ (254.4): Calcd.: C, 66.1; H, 10.3; N, 11.0. Found: C, 65.6; H, 10.6; N, 10.8.

EXAMPLE 3

N-(2,2,6,6,-tetramethylpiperidin-4-yl)-tetrahydro-3-phenyl-1,4-oxazin-2-one

A mixture of 26.9 g (0.134 mole) of the aminoalcohol used in Example 1, 30.8 g (0.134 mole) of methyl α-bromophenylacetate and 14.2 g of sodium carbonate in 100 ml N,N-dimethylformamide (DMF) is heated for six hours at 90° C. The solvent is removed by distillation and the residue partitioned between 300 ml ether and 100 ml water. The organic layer is extracted with 200 ml 1N hydrochloric acid. The acid extract is made alkaline with sodium carbonate and the product is taken into chloroform. The solvent is then evaporated and the product recrystallized from hexane to give 38 g (9% yield) of white solid, m.p. 78°-80° C.

Anal. $C_{19}H_{29}N_2O_2$ (316.4): Calcd.: C, 72.1; H, 8.9; N, 8.8. Found: C, 72.2; H, 8.9; N, 8.9.

EXAMPLE 4

N-(2,2,6,6-Tetramethylpiperidin-4-yl)-tetrahydro-3-n-dodecyl-1,4-oxazin-2-one

When the methyl α-bromophenylacetate of Example 3 is replaced by an equivalent amount of ethyl 2-bromomyristate, the above-named compound is obtained as a yellow viscous oil.

Anal. $C_{25}H_{48}N_2O_2$ (408.7): Calcd.: C, 73.5; H, 11.8; N, 6.9. Found: C, 73.4; H, 12.1; N, 6.5.

EXAMPLE 5

N-(2,2,6,6-Tetramethylpiperidin-4-yl)-tetrahydro-3-n-tetradecyl-1,4-oxazin-2-one When the ethyl 2-bromomyristate of Example 4 is replaced by an equivalent amount of ethyl 2-bromopalmitate, the above-named compound is obtained as a pale yellow clear syrup.

Anal. $C_{27}H_{52}N_2O_2$ (436.7): Calcd: C, 74.1; H, 12.0; N, 6.4. Found: C, 73.5; H, 12.1; N, 6.2.

EXAMPLE 6

Polypropylene (Hercules Profax 6501) containing a 0.1% by weight of calcium stearate, but no antioxidant, is blended with the instant light stabilizers. The mixture is pelletized and extruded at 450° F. (232° C.) into 4 inch (10.2 cm) tape with a thickness of 5 mil (0.127 mm). The tape is out cut into ¼ inch (6.4 mm) wide strips which are then stretched by a 6:1 ratio over Godet rolls at a temperature of 225° F. (107° C.) to give a stretched film tape of 2 mil (0.0508 mm) thickness.

The tape is subjected to light exposure in the carbon arc Weatherometer. After exposure, specimen tensile properties are determined with the hours to failure being taken as the time (hours) required for the tensile strength value to fall to 50% of the initial value.

The results are given in the table.

| Polypropylene plus 0.1% by weight light Stabilizer of Example No. | Hours to Failure (50% Retention of Tenacity) Carbon Arc Weatherometer |
| --- | --- |
| no light stabilizer | 230 |
| 2,4-dihydroxy-benzophenone | 240 |
| 1 | 2510 |

EXAMPLE 7

Accelerated UV Light Exposure Testing

Polypropylene powder (Hercules Profax 6401) is thoroughly blended with 0.2% by weight of the antioxidant, di(n-octadecyl) 3,5-di-tert-butyl-4-hydroxybenzylphosphonate, which prevents oxidative degradation of polypropylene during processing and with 0.25% of a light stabilizer being tested. The blended materials are then milled on a two-roll mill at 182° C. for 5 minutes after which time the stabilized polypropylene is sheeted from the mill and allowed to cool.

The milled polypropylene sheets are cut into pieces and processed for 3 minutes on a hydraulic press at 220° C. and 175 psi (12.3 Kg/cm$^2$) pressure. The resulting sheet of 5 mil (0.127 mm) thickness is water cooled in the press.

The 5 mil (0.127 mm) film is tested in a fluorescent sunlight black light environment with the development of carbonyl absorption in the infrared spectrum at the 5.85 micron wavelength being the measure of stabilization protection afforded by the stabilizers present in the polypropylene.

Failure is taken as the hours required to cause the carbonyl absorption to reach a value of 0.5. Such a value correlates with the reduction of physical properties of the polypropylene pellicle to unacceptable levels and is proportional to the amount of degradation caused by the ultraviolet light exposure.

The results are set out in Table A.

TABLE A

| Polypropylene plus 0.2% by weight antioxidant* plus 0.25% by weight light stabilizer of Example No. | Fluorescent Sunlight Black Light Test Hours to Failure (0.5 Carbonyl Absorption) |
| --- | --- |
| (First Series)** | |
| No light stabilizer (control) | 520 |
| 1 | 3030 |
| (Second Series)** | |
| No light stabilizer (control) | 390 |
| 2 | 1270 |
| 3 | 1120 |

*antioxidant is di(n-octadecyl) 3,5-di-tert-butyl-4-hydroxy-benzylphosphonate.
**These tests are run at two different times (different series of tests). The control values are not identical, but are similar and indicate the normal variation in values expected in this test.

What is claimed is:
1. A light stabilizer compound of the formula I

L—T wherein
L is a tetrahydro-1,4-oxazin-2-one group of the formula

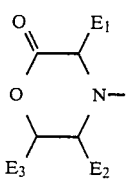

$E_1$ is hydrogen, alkyl of 1 to 16 carbon atoms or phenyl,
$E_2$ is hydrogen, alkyl of 1 to 4 carbon atoms or phenyl, $E_3$ is hydrogen or methyl, T is a group of the formula

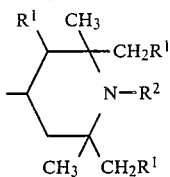

with L attached to the 4-position of the piperidinyl ring, $R^1$ is hydrogen or alkyl of 1 to 5 carbon atoms, and $R^2$ is hydrogen, oxygen, hydroxyl, alkyl of 1 to 12 carbon atoms, alkenyl with 3 to 8 carbon atoms, propargyl, benzyl, cyano, hydroxyalkyl of 2 to 4 carbon atoms, alkanoyl of 2 to 10 carbon atoms, alkenoyl of 3 to 4 carbon atoms, benzoyl, alkoxy of 1 to 8 carbon atoms, alkanoyloxy of 2 to 10 carbon atoms, alkenoyloxy of 3 to 4 carbon atoms or benzoyloxy.

2. A compound according to claim 1, where in the group L, $E_2$ is hydrogen.

3. A compound according to claim 1, where in the group L, $E_1$, $E_2$ and $E_3$ are each hydrogen.

4. A compound according to claim 1, where in the group T, $R^1$ is hydrogen or methyl.

5. A compound according to claim 4 wherein $R^1$ is hydrogen.

6. A compound according to claim 1 wherein $R^2$ is hydrogen, oxygen, hydroxyl, alkyl of 1 to 4 carbon atoms, allyl, 2-hydroxyethyl, acetyl, propargyl, benzyl, cyano, benzoyl or benzoyloxy.

7. The compound according to claim 1 which is N-(2,2,6,6-tetramethylpiperidin-4-yl)-tetrahydro-1,4-oxazin-2-one.

8. The compound according to claim 1 which is N-(2,2,6,6-tetramethylpiperidin-4-yl)-tetrahydro-6-methyl-1,4-oxazin-2-one.

9. The compound according to claim 1 which is N-(2,2,6,6-tetramethylpiperidin-4-yl)-tetrahydro-3-phenyl-1,4-oxazin-2-one.

10. The compound according to claim 1 which is N-(2,2,6,6-tetramethylpiperidin-4-yl)-tetrahydro-3-n-dodecyl-1,4-oxazin-2-one.

11. The compound according to claim 1 which is N-(2,2,6,6-tetramethylpiperidin-4-yl)-tetrahydro-3-n-tetradecyl-1,4-oxazin-2-one.

12. A composition of matter comprising an organic material subject to light-induced deterioration stabilized with from 0.05 to 5% by weight of a compound according to claim 1.

13. A composition according to claim 12 in which the organic material is a polyolefin.

14. A composition according to claim 13 in which the polyolefin is polyethylene or polypropylene.

15. A composition according to claim 12 wherein the compound is N-(2,2,6,6-tetramethylpiperidin-4-yl)-tetrahydro-1,4-oxazin-2-one.

16. A method of stabilizing an organic material subject to light-induced deterioration which comprises adding to said material from 0.05 to 5% by weight of a compound according to claim 1.

17. A method according to claim 16 in which the organic material is a polyolefin.

18. A method according to claim 17 in which the polyolefin is polyethylene or polypropylene.

19. A method according to claim 16 wherein the compound is N-(2,2,6,6-tetramethylpiperidin-4-yl)-tetrahydro-1,4-oxazin-2-one.

* * * * *